United States Patent [19]

Wootton

[11] 4,119,726
[45] Oct. 10, 1978

[54] CYCLIC EXO AMIDES

[75] Inventor: Gordon Wootton, Sawbridgeworth, England

[73] Assignee: Beecham Group Limited, United Kingdom

[21] Appl. No.: 796,715

[22] Filed: May 13, 1977

[30] Foreign Application Priority Data

May 22, 1976 [GB] United Kingdom .............. 21305/76

[51] Int. Cl.$^2$ .................. C07D 207/24; A61K 31/40; C07D 207/12
[52] U.S. Cl. .............................. 424/274; 260/293.56; 260/293.62; 260/293.72; 260/293.8; 260/293.81; 260/293.82; 260/293.83; 260/293.84; 260/293.88; 260/326.2; 260/326.47; 424/267
[58] Field of Search ....................... 260/326.2, 326.47; 424/274

[56] References Cited

U.S. PATENT DOCUMENTS

| | | | |
|---|---|---|---|
| 3,975,399 | 8/1976 | DeFreenco et al. | 260/326.2 |
| 4,003,911 | 1/1977 | Scribner | 260/326.47 |

Primary Examiner—Donald G. Daus
Assistant Examiner—Mary C. Vaughn
Attorney, Agent, or Firm—Jacobs & Jacobs

[57] ABSTRACT

Compounds of formula (I):

(I)

wherein:
$m$ is 0 or 1;
$n$ is 4 to 8;
X is CO, protected CO, CROH in which R is hydrogen or $C_{1-4}$ alkyl and in which the OH moiety may be protected;
$R_1$ is hydrogen, or $CO_2R_1$ represents an ester group in which the $R_1$ moiety contains 1 to 12 carbon atoms;
$R_3$ is hydroxy or protected hydroxy;
$R_2$ and $R_4$ are separately hydrogen, $C_{1-9}$ alkyl, $C_{5-8}$ cycloalkyl, $C_{5-8}$ cycloalkyl-$C_{1-6}$ alkyl, phenyl, phenyl $C_{1-6}$ alkyl, naphthyl, naphthyl $C_{1-6}$ alkyl, any of which phenyl or naphthyl moieties may be substituted by one or more halogen, trifluoromethyl, $C_{1-6}$ alkyl, $C_{1-6}$ alkoxy or nitro groups, or $R_2$ and $R_4$ taken with the carbon atom to which they are joined represent $C_{5-8}$ cycloalkyl;
$R_5$ is hydrogen, $C_{1-4}$ alkyl or phenyl; and salts thereof; have useful pharmacological properties including anti-gastric secretion, bronchodilator and platelet aggregation inhibition activities.

29 Claims, No Drawings

CYCLIC EXO AMIDES

This invention relates to novel compounds having pharmacological activity, to processes for their preparation, to intermediates useful in that process and to pharmaceutical compositions containing them.

More specifically the invention relates to piperidines and pyrrolidines acylated at nitrogen by an aliphatic or aliphatic aromatic group and substituted at an α-carbon atom by an aliphatic group.

Natural prostaglandins and analogues thereof are known to possess a wide variety of pharmacological activities.

Offenlegungsschrift No. 2,323,193 discloses that pyrazolidine derivatives of the formula (I)':

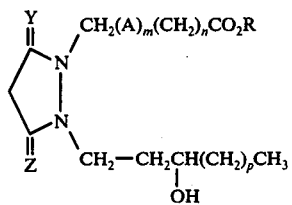

wherein A is CH=CH or C≡C; R is H, an alkali metal, an amine salt, or an γ 12C hydrocarbon or chlorohydrocarbon residue; $m$ is 0 or 1; $n$ is 0-6; $p$ is 0-6; and Y and Z are O or $H_2$ except that Y and Z are not both O; have similar biological properties to the prostaglandins or are antagonists of prostaglandins.

Japanese Patent Application No. 51,001,461 discloses the preparation of a compound of formula (II):

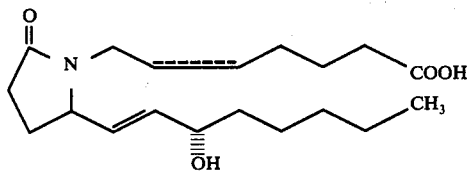

and states that this compound has laxative activity.

A novel class of compounds having useful pharmacological activity has now been discovered, which compounds are structurally distinct from the known compounds referred to above.

The present invention provides a compound of the formula (I):

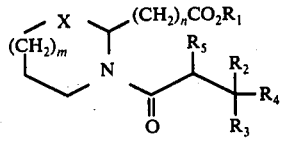

wherein:
$m$ is 0 or 1;
$n$ is 4 to 8;
X is CO, protected CO, CROH in which R is hydrogen $C_{1-4}$ alkyl and in which the OH moiety may be protected;
$R_1$ is hydrogen, or $CO_2R_1$ represents an ester group in which the $R_1$ moiety contains 1 to 12 carbon atoms;
$R_3$ is hydroxy or protected hydroxy;
$R_2$ and $R_4$ are separately hydrogen, $C_{1-9}$ alkyl, $C_{5-8}$ cycloalkyl, $C_{5-8}$ cycloalkyl - $C_{1-6}$ alkyl, phenyl, phenyl $C_{1-6}$ alkyl, naphthyl, naphthyl $C_{1-6}$ alkyl, any of which phenyl or naphthyl noieties may be substituted by one or more halogen, trifluoromethyl, $C_{1-6}$ alkyl, $C_{1-6}$ alkoxy or nitro groups; or
$R_2$ and $R_4$ taken with the carbon atom to which they are joined represent $C_{5-8}$ cycloalkyl;
$R_5$ is hydrogen, $C_{1-4}$ alkyl or phenyl; and salts thereof.

It is normally preferred that $m$ is 0.

Suitably $n$ is 5,6 or 7, preferably 6.

Suitably protected hydroxyl groups CROH and $R_3$ include readily hydrolysable groups such as acylated hydroxy groups in which the acyl moiety contains 1 to 4 carbon atoms, for example the acetoxy group; and hydroxy groups etherified by readily removable inert groups such as the benzyl or like groups. Preferably $R_3$ is hydroxy, and the hydroxy moiety in CROH is unprotected.

Suitable protected CO groups X include groups formed by conventional carbonyl addition and condensation reactions such as ketals, thioketals, hemithioketals, oximes, semicarbazones, hydrazones and the like. Of such groups often the ketal type derivatives will be most useful, for example when X is a group

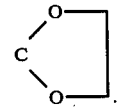

Examples of suitable groups X include CO, CHOH, $C(CH_3)OH$ and $C(C_2H_5)OH$. Preferably X is CO, CHOH or $C(CH_3)OH$, most preferably CO.

$R_1$ is hydrogen or $CO_2R_1$ represents an ester group in which the $R_1$ moiety contains from 1 to 12 carbon atoms. Examples of $R_1$ include hydrogen, methyl, ethyl, propyl, butyl, phenyl, benzyl, toluyl, and the like, while normally hydrogen or $C_{1-4}$ alkyl groups are preferred.

Preferably $R_3$ is hydroxy.

Suitable groups $R_2$ or $R_4$ when $R_2$ or $R_4$ is an alkyl group include $C_{4-9}$ alkyl groups. Such $C_{4-9}$ alkyl groups may be straight chain alkyl groups, such as n-butyl, n-pentyl, n-hexyl and n-heptyl, or may be alkyl groups branched by one or two methyl groups (at the same or different carbon atoms). Thus for example, $R_2$ or $R_4$ may be a group $CH_2R_6$, $CH(CH_3)R_6$ or $C(CH_3)_2R_6$, wherein $R_6$ is a straight chain alkyl group such that the carbon atom content of the resultant group $R_2$ or $R_4$ is 4 to 9.

In general preferred groups $R_2/R_4$ when $R_2/R_4$ is an alkyl group include straight chain pentyl, hexyl and heptyl groups. Of these, straight chain hexyl is often the most useful. However particularly preferred $R_2$ groups also include hydrogen, and $C_{1-4}$ alkyl groups such as hydrogen, methyl and ethyl.

When $R_2/R_4$ is or contains a $C_{5-8}$ cycloalkyl moeity, the moiety is suitably a cyclohexyl moiety. Examples of suitable $C_{1-6}$ alkyl moieties when $R_4$ is a $C_{5-8}$ cycloalkyl - $C_{1-6}$ alkyl group include methyl, ethyl, propyl, butyl and amyl.

$R_2$ and $R_4$ taken with the carbon atom to which they are joined may also represent $C_{5-8}$ cycloalkyl. Preferably this cycloalkyl group is cyclohexyl.

When $R_2/R_4$ is an aryl group as previously defined, suitable groups $R_2/R_4$ include phenyl, phenylmethyl, phenylethyl, phenyl n-propyl, phenyl n-butyl, naphthyl, naphthylmethyl, naphthylethyl, naphthyl n-propyl and naphthyl n-butyl. These groups may be substituted in the phenyl or naphthyl moiety by normally one, two or three groups selected from those substituent groups listed herein before. Examples of suitable substituent groups include fluorine, chlorine and bromine atoms and $CF_3$, methyl, ethyl, n- and iso-propyl, methoxy and ethoxy, n- and iso-propoxy and nitro groups.

Examples of suitable groups $R_5$ include hydrogen, methyl, ethyl, n- and iso-propyl and phenyl. Preferably $R_5$ is hydrogen, methyl or ethyl.

The compounds of the formula (I) may form conventional acid salts when $R_1$ is hydrogen. Such salts include those with alkali and alkaline earth metals, suitably sodium and potassium, and ammonium and substituted ammonium salts.

One group of compounds within formula (I) of particular interest due to their activity is of formula (II):

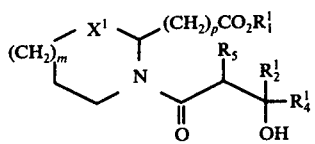
(II)

wherein:
  m is 0 or 1;
  p is 5,6 or 7;
  $X^1$ is CO, protected CO, CHOH or $C(CH_3)OH$;
  $R_1^1$ is hydrogen or $C_{1-4}$ alkyl;
  $R_2^1$ is hydrogen or $C_{1-3}$ alkyl;
  $R_4^1$ is $C_{4-9}$ alkyl, or a group of formula (III) (IV) or (V) as defined below:

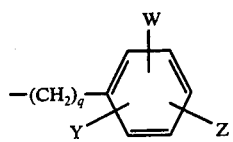
(III)

or:

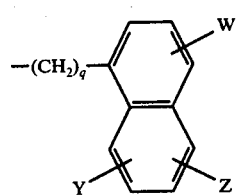
(IV)

or:

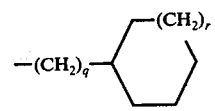
(V)

wherein:
  q is 0 to 5;
  r is 0 to 3; and
  W, Y, Z are separately hydrogen, fluorine, chlorine, bromine, $CF_3$, methyl, ethyl, n- or iso-propyl, methoxy, ethoxy, n- or iso-propoxy or nitro groups;
  $R_5$ is hydrogen, $C_{1-4}$ alkyl or phenyl; and salts thereof.

In formula (II) it is generally preferred that m is 0. P is most suitably 6.

$X^1$ is preferably CO, protected CO or CHOH, most preferably CO.

$R_2^1$ is suitably hydrogen, methyl or ethyl, preferably methyl or ethyl.

Suitable and preferred groups $R_4^1$ when $R_4^1$ is a $C_{4-9}$ alkyl group include those stated to be suitable and preferred alkyl groups for $R_4$. Examples of such groups include pentyl, hexyl, and heptyl groups, straight chain or branched by a methyl group.

When $R_4^1$ is a group of formula (III), (IV) or (V), then one or two of W, Y and Z are normally hydrogen, and r is normally 1.

$R_5$ is suitably hydrogen, methyl or ethyl.

A second group of compounds within formula (I) is of formula (VI):

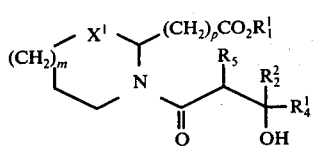
(VI)

wherein:
  m, p, $X^1$, $R_1^1$, $R_4^1$ and $R_5$ are as defined in formula (II), and
  $R_2^2$ is a group within those defined in formula (II) for $R_4^1$; or
  $R_2^2$ and $R_4^1$ together with the carbon atom to which they are joined represent $C_{5-8}$ cycloalkyl; and salts thereof.

Suitable and preferred values for the variables m, p, $R_1^1$, $X'$, $R_4^1$ and $R_5$ are as described in relation to formula (II).

Suitable and preferred values for $R_2^2$ are as described for $R_4^1$ in relation to formula (II).

The invention also provides a process for the preparation of a compound of the formula (I), which process comprises decarboxylating a compound of the formula (VII):

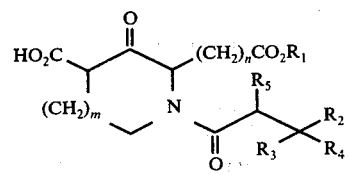
(VII)

wherein m, n, $R_1$, $R_2$, $R_3$, $R_4$ and $R_5$ are as defined in formula (I), to yield a compound of the formula (I) wherein X is CO; and thereafter if desired converting X in the thus formed compound to protected CO by conventional methods, or to CROH by reduction when R is hydrogen or by reaction with a $C_{1-4}$ alkyl Grignard reagent or $C_{1-4}$ alkyl metallic complex when R is $C_{1-4}$ alkyl, and then optionally protecting the CROH hydroxy moiety.

The decarboxylation reaction may be brought about under basic, acid or neutral conditions in conventional manner. For example when m = 0 the reaction is conveniently effected by heating the chosen compound of the formula (VII) in a suitable solvent having a suitable boiling point such as toluene, xylene, or DMF.

After the reaction $R_1$ may be varied by conventional deesterification and/or esterification reactions. Similarly protected CROH and $R_3$ hydroxy moieties may be deprotected by conventional methods. For example, when $R_3$ is a benzyloxy group, the benzyl group may readily be removed by hydrogenolysis. Thus it may be seen that 'protected hydroxy' compounds of the formula (I) are useful intermediates in the preparation of the corresponding 'free hydroxy' compounds of the formula (I).

The conversion of a compound of the formula (I) wherein X is CO to the corresponding compound wherein X is CHOH may be carried out by conventional methods for reducing a ketone to an alcohol, for example by sodium borohydride reduction.

The conversion of a compound of the formula (I) wherein X is CO to the corresponding compound wherein X is CROH in which R is $C_{1-4}$ alkyl may be carried out by conventional Grignard or alkyl metal, (suitably alkyl lithium) reactions.

When $R_1$ is hydrogen, salts of compounds of the formula (I) may be prepared in conventional manner, for example by reacting the chosen compound of the formula (I) with the required base.

It is frequently convenient however to generate the desired compound of the formula (I) directly from an ester of the formula (VIII), and often this will in fact be the preferred route:

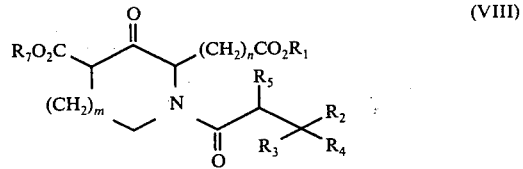
(VIII)

where $CO_2R_7$ is a conventional ester group. In such a case $R_7$ is preferably a benzyl group or a lower alkyl group such as ethyl or the like. Thus treatment of a compound of the formula (VIII) with, for example, lithium iodide dihydrate in anhydrous solvents brings about simultaneous de-esterification and decarboxylation.

It will be appreciated that compounds of the formulae (VII) and (VIII) are useful intermediates and as such form a useful aspect of this invention.

The compounds of formula (VIII) may be prepared by the ring closure of the corresponding triester of formula (IX):

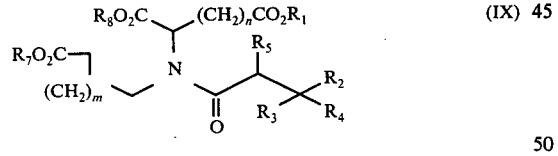
(IX)

wherein $m$, $n$, $R_1$, $R_2$, $R_3$ and $R_4$ are as defined in formula (I), $R_7$ is as defined in formula (VIII), and $R_8$ is a group such that $CO_2R_8$ is an ester group.

In the process of the invention the group $CO_2R_1$ in the intermediates of formula (VII), (VIII) and (IX) will normally represent an ester group, and if acids of the formula (I) (wherein $R_1$ is hydrogen) are required they will be obtained by de-esterification of the corresponding compound of the formula (I) wherein $CO_2R_1$ is an ester group. Usually the ester group $CO_2R_8$ in formula (IX) will be the same ester group as $CO_2R_1$, and for the sake of convenience the ester group $CO_2R_7$ will also normally be the same ester group as $CO_2R_1$. The ester groups $CO_2R_1/R_7/R_8$ are suitably $C_{1-4}$ alkyl esters such as methyl and ethyl esters.

Generally, the ring closure takes place in a dry organic solvent using a strong base such as sodium hydride or sodium ethoxide (or other $OR_7$ or $OR_8$ group) to bring about the initial proton abstraction from the α-methylene group.

It has been found that sodium ethoxide in benzene, or potassium t-butoxide in toluene, benzene or hexamethylphosphoramide give good results.

Compounds of formula (IX) are novel useful intermediates and as such, form an aspect of this invention.

Compounds of the formula (IX) may be prepared by the acylation of a compound of the formula (X):

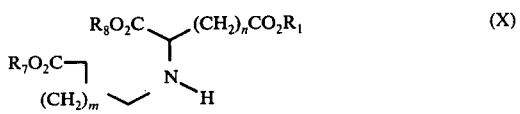
(X)

with a compound of the formula (XI):

(XI)

This acylation may be carried out by conventional acylation techniques, for example by using activated derivatives of (XI). Most suitably the acylation is carried out by using dicyclohexyl carbodiimide (DCC) as coupling agent.

The acid of formula (XI) may be prepared by conventional methods. It has been found that the following reaction scheme is particularly suitable:

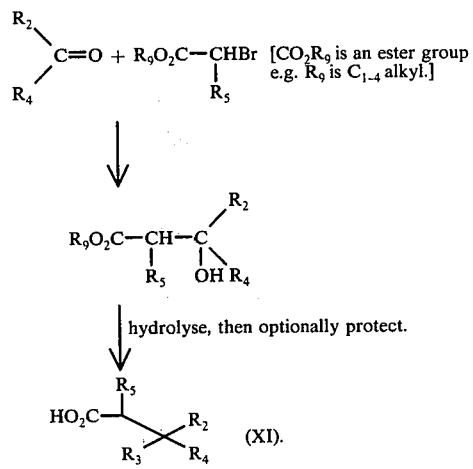

The amine of formula (X) may be prepared by reacting a compound of formula (XII):

(XII)

wherein Y is a halogen atom such as bromine, with an amino acid ester of formula (XIII):

(XIII)

$$R_7O_2C - CH_2 - (CH_2)_m - CH_2 - NH_2$$

The reaction is carried out in conventional manner for alkylation reactions of this nature.

Compounds within the formula (I) have useful pharmacological activity. For example compounds within formula (I) have anti-gastric secretion activity, cardiovascular activity, platelet aggregration inhibition activity, affect the respiratory tract e.g., bronchodilator activity, and have anti-fertility and smooth muscle activity.

In general it may be said that compounds within the formula (I) have a range of pharmacological activities similar to those shown by the natural prostaglandins, but that these activities tend to be rather more selective.

The invention therefore also provides a pharmaceutical composition comprising a compound of the formula (I) and a pharmaceutically acceptable carrier.

The formulation of the said pharmaceutical compositions will depend on the nature of the activity shown by the chosen compound of the formula (I), and on other factors such as a preference in a particular area of therapy for a particular mode of administration. In general however, the compositions may be formulated for administration by any route.

The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs or may be presented as a dry product for reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents, and the like.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anesthetic, preservatives and buffering agents can be dissolved in the vehicle. Parenteral suspensions are prepared in substantially the same manner except that the compound is suspended in the vehicle, instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

When appropriate, the compositions of this invention may be presented as an aerosol for oral administration, or as a microfine powder for insufflation.

As is common practice, the compositions will usually be accompanied by written or printed directions for use in the medical treatment concerned.

It will of course be realized that the precise dosage used in the treatment of any of the hereinbefore described disorders will depend on the actual compound of the formula (I) used, and also on other factors such as the seriousness of the disorder being treated.

It has been found that many of the compounds of the formula (I) are inhibitors of gastric secretion, and thus have commercial utility as anti-ulcer agents.

The invention also provides a method of treatment of disorders in human beings which comprises the administration to the sufferer of an effective amount of a compound of the formula (I).

It will of course be realised that the compounds of the formula (I) can have asymmetric centres, and thus are capable of existing in a number of stereoisomeric forms. The invention extends to each of these stereoisomeric forms, and to mixtures thereof. The different stereoisomeric forms may be separated one from the other by the usual methods.

The following Examples illustrate the invention:

EXAMPLE 1

(Compound 1)

Diethyl 2-[N-(2'-ethoxycarbonylethyl)] aminoazelate

Diethyl 2-bromoazelate (90g) in dry ethanol (50 ml) was added dropwise to a refluxing solution of β-alanine ethyl ester (35 g) in dry ethanol (175 ml) containing a suspension of sodium carbonate (35 g). Reflux was continued for 6 hours. When the reaction mixture cooled, the ethanolic solution was decanted, and the remaining solid was well washed with ether. The combined organic solutions were evaporated in vacuo and the residue was dissolved in ether. The ether solution was washed with brine than was dried over magnesium sulphate and evaporated to give a yellow oil (84.6g). The oil was vacuum distilled to remove unreacted starting materials but the residue was not further distilled as it tended to decompose. The diethyl 2-[N-(2'-ethoxycarbonylethyl)]aminoazelate (56g) was sufficiently pure for subsequent reactions and could be obtained analytically pure via column chromatography.

IR: 1730 cm$^{-1}$ [carbonyl of ester]

NMR: 6P($q$) at 5.9$\gamma$

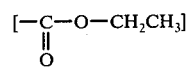

EXAMPLE 2

(Compound 2)

Ethyl 3-hydroxy-3-methyl-n-nonanoate

A portion (about 10%) of a mixture of ethyl 2-bromoacetate (75 g) and octan-2-one (64g) in dry benzene (100 ml) was added under nitrogen to dry zinc dust (37.5g). A few crystals of iodine were added to initiate the reaction. The stirrer was started and the remaining mixture of reactants was added, dropwise, at such a rate as to maintain reflux. External heat was applied to continue the reflux for 1½ hours after the final addition.

The cooled reaction mixture was treated with 20% sulphuric acid (200 ml) and the resulting two phases were separated. The aqueous phase was extracted once with benzene (200 ml). The combined benzene solution was washed with 5% sulphuric acid and with 10% sodium carbonate solution, then was dried over magnesium sulphate and evaporated in vacuo to give a clear oil. This was vacuum distilled to yield ethyl 3-hydroxy-3-methyl-n-nonanoate (25.1g).

N.B. No attempt was made to maximise the yield of this reaction.

B. pt. 85° at 0.2 mm. Hg.
IR: 3500 cm$^{-1}$ [OH] 1720 cm$^{-1}$ [carbonyl of ester]
NMR: 2P(q) at 5.85γ

[—C—OCH$_2$CH$_3$]
 ‖
 O

IP(s) at 6.72γ [OH]
2P(s) at 7.6γ [—CH$_2$CO$_2$Et]
The compounds shown in Table 1 were prepared in a similar manner.

TABLE 1

$$\text{EtO}_2\text{C}-\overset{R_5}{\underset{\phantom{X}}{\text{CH}}}-\overset{R_2}{\underset{\underset{R_4}{\text{HO}}}{\text{C}}}$$

| Compound | R$_5$ | R$_2$ | R$_4$ |
|---|---|---|---|
| 3 | H | CH$_3$ | CH$_2$CH$_2$Ph |
| 4 | H | CH$_3$ | Ph |
| 5 | H | CH$_3$ | CH(CH$_3$)C$_4$H$_9$ |
| 6 | H | | 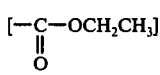 |

Compound 3: B. Pt. 120° at 0.3 mm Hg.
  IR: 3500 cm$^{-1}$ [OH]; 1710 (carbonyl(of ester)]
  NMR: 5P(s) at 2.8τ [Ph]; 2P(q) at 5.8τ [—C—OCH$_2$CH$_3$]
                                          ‖
                                          O
    1P(s) at 6.5τ [OH]; 2P(m) at 7.2τ [—CH$_2$Ph]
    2P(s) at 7.5τ [—CH$_2$CO$_2$Et]
Compound 4: B. pt. 97° at 0.3 mm Hg.
  IR: 3500 cm$^{-1}$ [OH]; 1710 cm$^{-1}$ [carbonyl of ester]
  NMR: 5P(m) at 2.7τ [Ph]; 1P(s) at 5.85τ [OH];
    2P(q) at 5.95τ [—C—OCH$_2$CH$_3$];
    2P(d) at 7.25τ [—CH$_2$CO$_2$Et]
    3P(s) at 8.05τ [CH$_3$];
    3P(t) at 8.9τ [—C—OCH$_2$CH$_3$]
Compound 5: B. Pt. 84° at 0.06 mm. Hg.
  IR: 3500 cm$^{-1}$ [OH]; 1710 cm$^{-1}$ [carbonyl(of ester)]
  NMR: 2P(q) at 5.85τ [—C—OCH$_2$CH$_3$];
                      ‖
                      O
    1P(s) at 6.7τ [OH]
    2P(s) at 7.6τ [—CH$_2$CO$_2$Et]
Compound 6: B. Pt. 90° at 0.05 mm.
  IR: 3500 cm$^{-1}$ [OH]; 1710 cm$^{-1}$ [carbonyl(of ester)]
  NMR: 2P(q) at 5.8τ [—C—OCH$_2$CH$_3$];
                     ‖
                     O
    1P(s) at 6.7τ [OH]
    2P(s) at 7.55τ [—CH$_2$CO$_2$Et]

EXAMPLE 3

(Compound 7)

3-Hydroxy-3-methyl-n-nonanoic acid

Ethyl-3-hydroxy-3-methyl-n-nonanoate (25 g) was refluxed for 3 hours with a 10% solution of potassium hydroxide in dry ethanol (210 ml). The ethanol was evaporated in vacuo and the residue was treated with water (100 ml). The aqueous solution was washed with ether then was acidified (ice-bath cooling) with dilute hydrochloric acid. The oil that separated was extracted into ether. The ether solution was washed with brine then was dried over magnesium sulphate and evaporated to give a light yellow oil. This was vacuum distilled to yield 3-hydroxy-3-methyl-n-nonanoic acid as a clear syrup (18.1g).
B. Pt. 130° at 0.25 mm Hg.
IR: Broad band 3100 to 2400 cm$^{-1}$ [CO$_2$H]
Broad band at 1700 cm$^{-1}$ [carbonyl of acid]
NMR: 2P(s) at 2.17γ [—CO$_2$H; OH]

2P(s) at 7.5γ [—CH$_2$CO$_2$H]
The compounds shown in Table 2 were prepared in a similar manner.

TABLE 2

$$\text{HO}_2\text{CCHC}\overset{R_5\phantom{XX}R_2}{\underset{\underset{R_4}{\text{HO}}}{\diagup}}$$

| Compound | R | R$_2$ | R$_4$ |
|---|---|---|---|
| 8 | H | CH$_3$ | CH$_2$CH$_2$Ph |
| 9 | H | CH$_3$ | Ph |
| 10 | H | CH$_3$ | CH(CH$_3$)C$_4$H$_9$ |
| 11 | H | |  |

Compound 8: B.Pt. 130° at 0.25 mm. Hg.
  IR: 3700 to 2400 cm$^{-1}$ [—CO$_2$H]; 1710 cm$^{-1}$ [carbonyl (of acid)]
  NMR: 2P(s) at 2.15τ [CO$_2$H + OH]; 2P(s) at 7.5γ [—CH$_2$CO$_2$H]
Compound 9:
  IR: 3700 to 2400 cm$^{-1}$ [CO$_2$H]; 1690 cm$^{-1}$ [carbonyl (of acid)]
Compound 10:
  IR: 3700 to 2400 cm$^{-1}$ [CO$_2$H]; 1700 cm$^{-1}$ [carbonyl (of acid)]
  NMR: 2P(S) at 2.6τ [CO$_2$H + OH]; 5P(s) at 2.75τ [Ph]
    2P(broad s) at 7.2τ [—CH$_2$CO$_2$H]; 3P(s) at 8.55τ [CH$_3$]
Compound 11:
  IR
  NMR: 2P(s) at 2.6τ [CO$_2$H + OH]; 2P(s) at 7.5γ [CH$_2$CO$_2$H]

EXAMPLE 4

(Compound 12)

Diethyl 2-[N-(2'-ethoxycarbonylethyl)-N-(3''-hydroxy-3''-methyl-n-nonanoyl)]aminoazelate Dicyclohexylcarbodi-imide (10.3g) in dry dichloromethane (50 ml) was added dropwise to a stirred, ice-cold, mixture of 3-hydroxy-3-methyl-n-nonanoic acid (9.4g) and diethyl 2-[N-(2-ethoxycarbonylethyl)-]aminoazelate (17.98g) in dry dichloromethane (150 ml). The mixture was allowed to warm to room temperature and stirring was continued overnight. The dicyclohexylurea was filtered off; the filtrate was evaporated in vacuo and the residue was dissolved in ether. The ether solution was washed with 5% sodium bicarbonate solution and with brine then was evaporated in vacuo to give diethyl 2-[N-(2'-ethoxycarbonylethyl)-N-(3''-hydroxy-3''-methyl-n-nonanoyl)] aminoazelate as a yellow oil (28.1g).
IR: 3400 cm$^{-1}$ [OH]; 1730, 1630 cm$^{-1}$ [carbonyl of ester and amide respectively].
The compounds shown in Table 3 were prepared in a similar manner.

TABLE 3

| Compound | n | R$_5$ | R$_2$ | R$_4$ |
|---|---|---|---|---|
| 13 | 6 | H | CH$_3$ | CH$_2$CH$_2$Ph |
| 14 | 6 | H | CH$_3$ | Ph |
| 15 | 6 | H | CH$_3$ | CH(CH$_3$)C$_4$H$_9$ |

TABLE 3-continued

| Compound | n | $R_5$ | $R_2$ | $R_4$ |
|---|---|---|---|---|
| 16 | 6 | H | | ⬡ |

Compound 13:
IR: 3400 cm$^{-1}$ [OH]; 1725, 1630 cm$^{-1}$ [carbonyls(of ester and amide respectively)]

Compound 14:
IR: 3400 cm$^{-1}$ [OH]; 1725, 1630 cm$^{-1}$ [carbonyls(of ester and amide respectively)]

Compound 15:
IR: 3400 cm$^{-1}$ [OH]; 1725, 1630 cm$^{-1}$ [carbonyls(of ester and amide respectively)]

NMR: 7P(m) at 5.9τ [3x-C(=O)-OCH$_2$CH$_3$ + 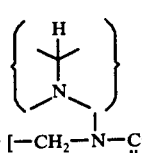

2P (unresolved m) at 6.5τ [—CH$_2$—N—C(=O)—]

Compound 16:
IR: 3450 cm$^{-1}$ [OH]; 1730, 1630 cm$^{-1}$ [carbonyls (of ester and amide respectively)]

NMR: 7P(m) at 5.9τ [3x-C(=O)-OCH$_2$CH$_3$ +

2P (unresolved m) at 6.5τ [—CH$_2$—N—C(=O)—]

EXAMPLE 5

(Compound 17)

1-(3'-Hydroxy-3'-methyl-n-nonanoyl)-2-(6"-ethoxycarbonyl-n-hexyl)-4-ethoxycarbonylpyrrolidin-3-one Diethyl 2-[N-(2'-ethoxycarbonylethyl)-N-(3"-hydroxy-3"-methyl-n-nonanoyl)] aminoazelate (1.06g) was refluxed with potassium tert butoxide (0.24g) in dry benzene (25 ml) for 1½ hours. The benzene was evaporated in vacuo and the residue was partitioned between very dilute hydrochloric acid and ether. The ether solution was washed with brine then was dried over magnesium sulphate and evaporated to give 1-(3'-hydroxy-3'-methyl-n-nonanoyl)-2-(6"-ethoxycarbonyl-n-hexyl)-4-ethoxycarbonylpyrrolidin-3-one as a pale yellow gum (800mg).

IR: 3370 cm$^{-1}$ [OH]; 1730, 1630 cm$^{-1}$ [carbonyls (of ester and amide respectively)]

The compounds shown in Table 4 were prepared in a similar manner.

TABLE 4

| Compound | n | $R_5$ | $R_2$ | $R_4$ |
|---|---|---|---|---|
| 18 | 6 | H | CH$_3$ | CH$_2$CH$_2$Ph |
| 19 | 6 | H | CH$_3$ | Ph |
| 20 | 6 | H | CH$_3$ | CH(CH$_3$)C$_4$H$_9$ |
| 21 | 6 | H | | ⬡ |

EXAMPLE 6

(Compound 22)

1-(3'-Hydroxy-3'-methyl-n-nonanoyl)-2-(6"-ethoxycarbonyl-n-hexyl)pyrrolidin-3-one 1-(3'-Hydroxy-3'-methyl-n-nonanoyl)-2-(6"-ethoxycarbonyl-n-hexyl)-4-ethoxycarbonylpyrrolidin-3-one (19g) was refluxed with lithium iodide dihydrate (9.5g) in dry dimethylformamide (400 ml) for 2½ hours. The dimethylformamide was evaporated in vacuo and the residual oil was partitioned between very dilute hydrochloric acid and ether. The ether solution was washed with 5% sodium bicarbonate solution and with brine then was dried over magnesium sulphate and evaporated in vacuo to give a thick dark oil. This was chromatographed on a column of kieselgel (20:1 ratio) using chloroform as eluent to give 1-(3'-hydroxy-3'-methyl-n-nonanoyl)-2-(6"-ethoxycarbonyl-n-hexyl)pyrrolidin-3-one (3.27g) as a mixture of isomers.

IR: 3300 [OH]; 1750, 1720, 1630 cm$^{-1}$ [carbonyls of ketone, ester and amide respectively]

The compounds shown in Table 5 were prepared in a similar manner and in the cases indicated, further chromatographic separation gave two observable isomers. [TLC system: 40% ethyl acetate, 60% petroleum ether - silica plates.]

TABLE 5

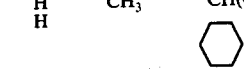

| Compound | n | $R_5$ | $R_2$ | $R_4$ |
|---|---|---|---|---|
| 23 | 6 | H | CH$_3$ | CH$_2$CH$_2$Ph |
| 24(a)(b) | 6 | H | CH$_3$ | Ph |
| 25(a)(b) | 6 | H | CH$_3$ | CH(CH$_3$)C$_4$H$_9$ |
| 26 | 6 | H | | ⬡ |

Compound 23
IR: 3300 cm$^{-1}$ [OH]; 1745, 1720, 1630 cm$^{-1}$ [carbonyls (of ketone, ester and amide respectively)]
NMR: 5P(s) at 2.9τ [Ph]; 1P(s) at 5.35τ [OH]
5P(m) at 5.5 to 6.5τ

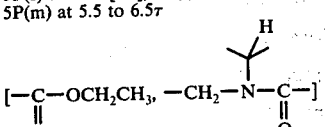

[—C(=O)—OCH$_2$CH$_3$, —CH$_2$—N—C(=O)—]

Mass Spec: Molecular ion at 431
Compound 24 (a) Lower $R_f$ isomer
IR: 3350 cm$^{-1}$ [OH]; 1740, 1715, 1610 cm$^{-1}$ [carbonyls (of ketone, ester and amide respectively)]
NMR: 5P(m) at 2.7τ [Ph]; 1P(s) at 4.45τ [OH]

TABLE 5-continued

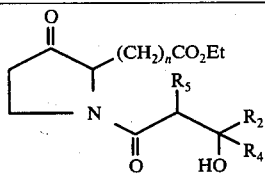

| Compound | n | R₅ | R₂ | R₄ |
|---|---|---|---|---|
| 5P(m) at 5.6 to 6.6τ | | | | |

NMR:

1P(s) at 4.8τ

2P(q) and 5P(m) at 5.7 to 6.8τ

4P(s+t) 7.7 to 8τ

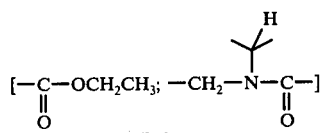

Compound 24 (b) Upper R/isomer
Data as for 24 (a)
Compound 25 (a) Upper R/isomer
IR:  3350 cm⁻¹ [OH]; 1750, 1730, 1630 cm⁻¹ [carbonyls ketone ester and amide respectively)]
NMR:  1P(s) at 5.35τ [OH]; 5P(m) at 5.6τ tp 6.6τ

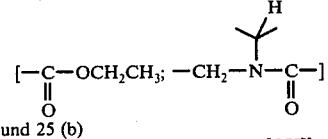

Compound 25 (b)
Data as for 25 (a) [NMR - 1P(s) at 5.4τ [OH]]
Compound 26
IR:  3400 cm⁻¹ [OH]; 1750, 1730, 1630 cm⁻¹ [carbonyls (of ketone, ester and amide respectively)]
NMR:  1P(d) at 5.55τ [OH]; 5P(m) at 5.7 to 6.6τ

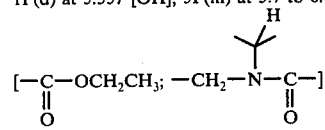

EXAMPLE 7

(Compound 27)

1-(3'-Hydroxy-3'-methyl-n-nonanoyl)-2-(6''-ethoxycarbonyl-n-hexyl)-3-hydroxypyrrolidine 1-(3'-Hydroxy-3'-methyl-n-nonanoyl)-2-(6''-ethoxycarbonyl-n-hexyl)pyrrolidin-3-one (1.46g) in dry ethanol (20 ml) was treated dropwise with portions of sodium borohydride (135 mg total) and the resulting solution was stirred at room temperature for 3 hours. The ethanol was evaporated in vacuo at room temperature and the residual oil was partitioned between very dilute hydrochloric acid and ether. The ether solution was washed with brine, dried over magnesium sulphate and evaporated in vacuo to give a yellow oil (1.17g). This was purified via column chromatography to give 1-(3'-hydroxy-3'-methyl-n-nonanoyl)-2-(6''-ethoxycarbonyl-n-hexyl)-3-hydroxypyrrolidine (530 mg) as a clear oil which solidified on standing.

IR: 3400 cm⁻¹ [OH]; 1730, 1620 [carbonyls (of ester and amide respectively)]; loss of ketonic carbonyl at 1750 cm⁻¹

Mass Spec. Molecular ion at 413.

The compounds in Table 6 were prepared in a similar manner.

TABLE 6

| Compound | n | R₅ | R₂ | R₄ |
|---|---|---|---|---|
| 28 | 6 | H | CH₃ | CH(CH₃)C₄H₉ |
| 29 | 6 | H | | ⬡ |

Compound 28
IR:  3450 cm⁻¹ [OH]; 1730, 1620 cm⁻¹ [carbonyls (of ester and amide respectively)] loss of ketonic carbonyl at 1750 cm⁻¹
NMR:  1P(d) at 4.7τ [OH]; 7P(m) at 5.5 to 6.7τ

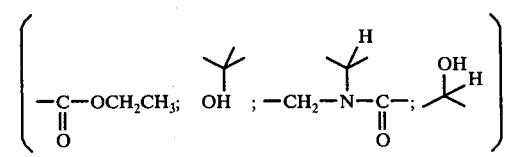

Mass Spec: Molecular ion at 413
Compound 29
IR:  3350 cm⁻¹ [OH]; 1720, 1610 cm⁻¹ [carbonyls (of ester and amide respectively)] loss of ketonic carbonyl at 1750 cm⁻¹
NMR:  1P(d) at 4.9τ [OH]; 7P (m) at 5.6 to 6.7τ

TABLE 6-continued

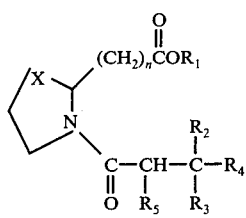

| Compound | n | R₅ | R₂ | R₄ |
|---|---|---|---|---|

$$\left(\begin{array}{l}-\underset{\underset{O}{\|}}{C}-OCH_2CH_3;\ -CH_2-\underset{\underset{O}{\|}}{N}-\underset{H}{\overset{H}{C}}-;\ H\diagdown\!\!\!\diagup^{OH}\ \diagdown\!\!\!\diagup^{OH}\end{array}\right)$$

Toxicity

No apparent side effects were observed after administration of Compound 22 at 100 mg/kg sub. cut. in the hamster and I.D. in the rat.

B290

Pharmacological Data

The compounds were examined for their ability to inhibit pentagastrin-stimulated gastric acid secretion in the anaesthetised, perfused rat stomach preparation (Ghosh and Schild preparation, ref: M. N. Ghosh and H. O. Schild, 1958, Brit. J. Pharmacol., 13, 54.)

Compound 25(a), the upper isomer, was active in this test in the dose range 500μg–10mg/kg, intra-venously, whereas the isomeric mixture of Compound 25(a) and 25(b) was active in the dose range 500μg–1mg/kg, intra-venously. Compound 26 was active in the dose range 10–20mg/kg, intra-venously.

The compounds were also examined for their ability to inhibit gastric acid secretion in the pyloric ligated rat model (Shay rat preparation, ref: H. Shay et al., 1945, Gastroenterology, 5, 43.

When given intra-duodenally at 200mg/kg the isomeric mixture of Compound 25(a) and 25(b) inhibited the total titratable acidity in the stomach by 92%. Compound 25(a) when given at 100mg/kg, intra-duodenally, lowered the acidity by 43%.

Toxicity

No apparent side effects were observed after administration of Compound 22 or Compound 25(a) at 100mg/kg, intra-duodenally, in the rat or of Compound 22 at 100mg/kg, subcutaneously, in the hamster.

What we claim is:

1. A compound selected from the group consisting of a cyclic exoamide of the formula:

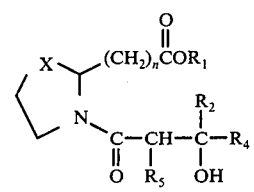

wherein
n has a value of 4 to 8;
X is carbonyl; a ketal, thioketal, hemithioketal, oxime, semicarbazone or hydrazone derived from such carbonyl; or C(OH)R in which R is hydrogen or alkyl of 1 to 4 carbon atoms;
$R_1$ is hydrogen, alkyl of 1 to 12 carbon atoms, phenyl, benzyl or toluyl;
$R_3$ is hydroxy, acyloxy of 1 to 4 carbon atoms, or benzyloxy;
each of $R_2$ and $R_4$ is independently hydrogen, alkyl of 1 to 9 carbon atoms, cycloalkyl of 5 to 8 carbon atoms, phenyl, naphthyl, or alkyl of 1 to 6 carbon atoms substituted with cycloalkyl of 5 to 8 carbon atoms, phenyl or naphthyl, said phenyl and naphthyl being unsubstituted or substituted by up to three substituents selected from the group consisting of fluoro, chloro, bromo, trifluoromethyl, alkyl of 1 to 4 carbon atoms, nitro, and alkoxy of 1 to 4 carbon atoms, or $R_2$ and $R_4$ taken together with the carbon atoms to which they are commonly bound are cycloalkyl of 5 to 8 carbon atoms; and
$R_5$ is hydrogen, alkyl of 1 to 4 carbon atoms or phenyl,
and the pharmaceutically acceptable non-toxic salts thereof.

2. A compound according to claim 1 wherein said cyclic exoamide is of the formula:

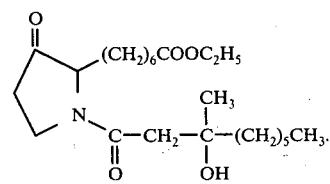

wherein
n has a value of 5, 6 or 7;
X is carbonyl, hydroxymethylene or 1-hydroxyethylidene;
$R_1$ is hydrogen or alkyl of 1 to 4 carbon atoms;
$R_2$ is hydrogen, methyl or ethyl;
$R_4$ is alkyl of 4 to 9 carbon atoms, phenyl or phenethyl; or
$R_2$ and $R_4$ taken together with the carbon atom to which they are commonly bound are cycloalkyl of 5 to 8 carbon atoms; and
$R_5$ is hydrogen, alkyl of 1 to 4 carbon atoms or phenyl.

3. A compound according to claim 2 wherein
X is carbonyl or hydroxymethylene;
$R_1$ is hydrogen or alkyl of 1 to 4 carbon atoms;
$R_2$ is methyl;
$R_4$ is alkyl of 1 to 6 carbon atoms, phenyl or phenethyl; and
$R_5$ is hydrogen.

4. A compound according to claim 1 wherein said cyclic exoamide is that depicted by the formula:

$$\begin{array}{c}\overset{O}{\underset{\|}{}} \\ \diagup\!\!\!\diagdown \ (CH_2)_6COOC_2H_5 \\ | \ \ \ | \\ \diagdown\!\!\!\diagup_{N\diagdown}\ \ \ \ \ CH_3 \\ \ \ \ \ \ \ \ \ \ \ \ \underset{\|}{C}-CH_2-\underset{|}{C}-(CH_2)_5CH_3. \\ \ \ \ \ \ \ \ \ \ \ \ O\ \ \ \ \ \ \ \ OH \end{array}$$

5. A compound according to claim 1 wherein said cyclic exoamide is that depicted by the formula:

6. A compound according to claim 1 wherein said cyclic exoamide is that depicted by the formula:

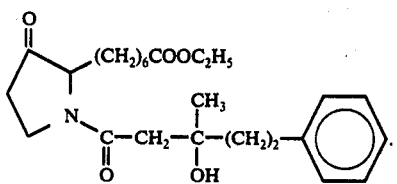

7. A compound according to claim 1 wherein said cyclic exoamide is that depicted by the formula:

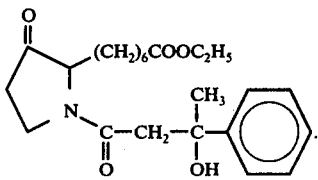

8. A compound according to claim 1 wherein said cyclic exoamide is that depicted by the formula:

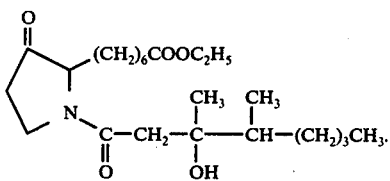

9. A compound according to claim 1 wherein said cyclic exoamide is that depicted by the formula:

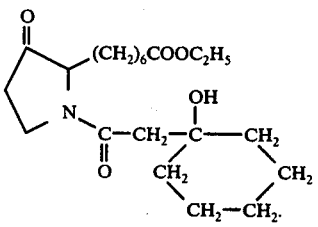

10. A compound according to claim 1 wherein said cyclic exoamide is that depicted by the formula:

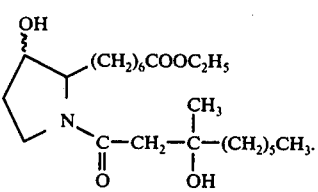

11. A compound according to claim 1 wherein said cyclic exoamide is that depicted by the formula:

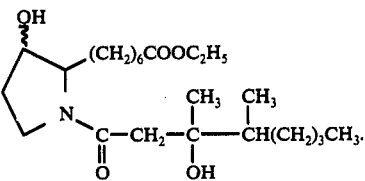

12. A compound according to claim 1 wherein X is carbonyl, hydroxymethylene or 1-hydroxyethylidene.

13. A compound according to claim 1 wherein $n$ is 5, 6, or 7.

14. A compound according to claim 1 wherein $R_1$ is hydrogen or alkyl of 1 to 4 carbon atoms.

15. A compound according to claim 1 wherein $R_2$ is hydrogen or alkyl of 1 to 4 carbon atoms.

16. A compound according to claim 1, wherein $R_3$ is hydroxy.

17. A compound according to claim 1 wherein $R_4$ is alkyl of 4 to 9 carbon atoms and having the structure $CH_2R_6$, $CH(CH_3)R_6$ or $C(CH_3)_2R_6$ wherein $R_6$ is straight chain alkyl.

18. A compound according to claim 1 wherein $R_4$ is phenylmethyl, phenylethyl, phenyl n-propyl, phenyl n-butyl, naphthyl, naphthylmethyl, naphthylethyl, naphthyl n-propyl, or naphthyl n-butyl unsubstituted or substituted in the phenyl or naphthyl ring by fluoro, chloro, bromo, trifluoromethyl, methyl, ethyl, n-propyl, iso-propyl, methoxy, ethoxy, n-isopropoxy isopropoxy, or nitro.

19. A compound according to claim 1 wherein $R_5$ is hydrogen, methyl or ethyl.

20. A compound according to claim 2, wherein $n$ is 6.

21. A compound according to claim 2 wherein wherein X is hydroxymethylene.

22. A compound according to claim 2, wherein X is carbonyl.

23. A compound according to claim 2, wherein $R_2$ is hydrogen.

24. A compound according to claim 2, wherein $R_2$ is methyl or ethyl.

25. A compound according to claim 2 wherein $R_4$ is alkyl of 4 to 9 carbon atoms.

26. A compound according to claim 2 wherein $R_4$ is n-pentyl, sec-pentyl, n-hexyl, sec-hexyl, n-heptyl or sec-heptyl.

27. A compound according to claim 1, wherein $R_5$ is hydrogen, methyl or ethyl.

28. A pharmaceutical composition for the treatment of gastric acid secretion, bronchodilation and platelet aggregation inhibition activities comprising a compound according to claim 1 in an amount sufficient to overcome such disorders and a pharmaceutically acceptable carrier.

29. A method of effecting a prostaglandin-like pharmaceutical response in human beings in need thereof which comprises administering an effective amount of a compound according to claim 1.

* * * * *